United States Patent [19]

Rüegg et al.

[11] 3,989,758
[45] Nov. 2, 1976

[54] MONOACETALS OF UNSATURATED ALIPHATIC DIALDEHYDES

[75] Inventors: Rudolf Rüegg, Bottmingen; Ulrich Schwieter, Reinach, both of Switzerland

[73] Assignee: Hoffmann-La Roche Inc., Nutley, N.J.

[22] Filed: Oct. 14, 1971

[21] Appl. No.: 189,411

Related U.S. Application Data

[62] Division of Ser. No. 808,664, March 19, 1969, Pat. No. 3,665,039, which is a division of Ser. No. 323,156, Nov. 12, 1963, Pat. No. 3,466,335.

[30] Foreign Application Priority Data
Nov. 16, 1962  Switzerland.................... 13430/62
May 17, 1963  Switzerland.................... 6208/63

[52] U.S. Cl............................. 260/602; 260/340.9; 260/338; 260/340.7
[51] Int. Cl.².................. C07D 47/20; C07W 307/26

[58] Field of Search................. 260/602, 338, 340.7, 260/340.9

[56] References Cited
OTHER PUBLICATIONS

Makin et al., "Chem. Abstracts," vol. 60, p. 10535c, (1964).
Baumgarten et al., "Berichte Der Deutschen Chem. Gesell.," vol. 66, p. 1802, (1933).
Schwieter et al., "Helv. Chimiea Acta," vol. 49, pp. 369 to 389, (1966).

*Primary Examiner*—Donald G. Daus
*Assistant Examiner*—D. B. Springer
*Attorney, Agent, or Firm*—Samuel L. Welt; Bernard S. Leon; Richard A. Gaither

[57] ABSTRACT

Mono acetals of unsaturated aliphatic dialdehydes having from 7 to 10 carbon atoms which are intermediates in the preparation of carotenoids.

5 Claims, No Drawings

MONOACETALS OF UNSATURATED ALIPHATIC DIALDEHYDES

CROSS REFERENCE TO RELATED APPLICATIONS

This application is a divisional application of Ser. No. 808,664 filed Mar. 19, 1969, now U.S. Pat. No. 3,665,039, issued May 23, 1975, which in turn is a divisional application of Ser. No. 323,156 filed Nov. 12, 1963, now U.S. Pat. No. 3,466,335, issued Aug. 9, 1969.

DETAILED DESCRIPTION OF THE INVENTION

The present invention relates to a process for the preparation of polyene compounds. In the synthetic preparation of vitamin A and also in the isolation of vitamin A from natural sources, the vitamin A active material can only partially be separated in the form of crystalline all-trans vitamin A from the mixtures which result from its preparation or isolation procedures. Even when the remaining mother liquors are subjected to complicated workup operations it is not possible according to the hitherto known procedures to isolate the material present in pure crystalline form to a satisfactory extent. These difficulties are largely due to the vitamin A active material being present in numerous isomeric forms, for example, as 13-cis-, 11-cis-, 11,13-di-cis-, 9-cis-, 9,13-di-cis- vitamin A or as anhydro vitamin A. The fact that these various isomers are not isomerizable or only isomerizable with difficulty is particularly aggravating. Hence, there remains, after the separation of crystalline all-trans vitamin A, a vitamin A active mixture containing various isomers for which, up to now, no economically satisfactory use has been found. This is true despite various attempts which have been made to utilize these mixtures.

There has now surprisingly been discovered a process by which the conversion of the difficulty crystallizable vitamin A isomeric mixture resulting from synthetic or extractive processes into definite crystalline compounds can be effected. The processes of the invention utilize triaryl-phosphonium salts, which are then reacted with unsaturated aldehydes to form valuable carotenoids. The carotenoids are formed by reacting difficulty crystallizable vitamin A active alcohols and/or lower alkyl esters thereof from the synthetic or extractive preparation of vitamin A or esters with a triaryl-phosphine in the presence of a proton donor or with an acid addition salt of a triaryl-phosphine; and the resulting triaryl-phosphonium salt is isolated in crystalline form, and then reacted with an unsaturated aldehyde with the addition of a proton acceptor.

The instant invention is applicable to all crude mixtures obtainable from the known vitamin A processes. By way of example, such crude mixtures are obtained in the known vitamin A syntheses mentioned below:

From 4-[2,6,6-trimethyl-cyclohexen-1-yl]-2-methyl-2-buten-1-al with 3-methyl-2-penten-4-yn-1-ol, Helv. Chim. Acta., 1947, 30, p. 1911 and Helv. Chim. Acta., 1949, 32, p. 489.

From β-ionylidene-ethyl-triphenyl-phosphonium halides and β-formyl-crotonic acid esters or γ-acyloxy-tiglinic aldehyde, Angew. Chemie, 1960, 72, p. 811.

From 6-[2,6,6-trimethyl-cyclohexen-1-yl]-4-methyl-4-hydroxy-5-hexen-1-yne or 6-[2,6,6-trimethyl-cyclohexen-1-yl]-4-methyl-3,5-hexadien-1-yne and keto-butanal diacetal, 3-keto-butanol diacotal, U.S. Pat. No. 2,676,992, Angew. Chemie, 1960, 72, p. 955.

From β-ionylidene acetaldehyde by condensation with acetone followed by condensation with cyanoacetic acid or esters thereof, D.A.S. No. 1,041,950.

From β-ionylidene acetaldehyde and senecioic acid esters, Journal of Vitaminology, 1958, 4, p. 178.

Also, concentrates obtained from natural sources (such as, for example, fish liver oils) can be reacted with success according to the process of the invention.

In the first step of the process of the invention, a crude mixture containing difficulty crystallizable vitamin A active alcohols and/or esters is advantageously reacted in the presence of an inert solvent (such as, for example, a lower alkanol such as methanol or ethanol) with a triaryl-phosphine in the presence of a proton donor or with an acid addition salt of a triaryl-phosphine. Proton donors which can be employed in the above process include inorganic acids, such as the hydrohalic acids (especially hydrochloric acid) or sulfuric acid. Moreover, all acids which form acid addition salts with triaryl-phosphines (e.g., strong organic acids such as benzenesulfonic acid or trichloro-acetic acid) as well as those specifically named above can also be employed. Triaryl-phosphines which can be employed include triphenyl-phosphine, tritolyl-phosphine, diphenyl-tolyl-phosphine and tri-p-methoxyphenyl-phosphine, with triphenyl-phosphine preferred. When an acid addition salt of a triaryl-phosphine is employed, the acid used to form the acid addition salt can be a pharmaceutically acceptable strong acid such as the mineral acids and strong organic acids such as the sulfonic acids, e.g., benzene- and toluenesulfonic acid, etc. Non-pharmaceutically acceptable strong acids can also be employed, since the salt is not present in the final carotenoid product, although the salts of pharmaceutically acceptable strong acids are preferred.

The triaryl-phosphonium salt formed can be enriched in the reaction mixture by removing the non-polar portions thereof. This can be effected, for example, by distribution between an aqueous alcohol (such as methanol or ethanol) and a non-polar solvent which is immiscible with the aqueous alcohol (such as petroleum ether). For the distribution there is advantageously used a methanol (or ethanol)/petroleum ether mixture consisting of about 70 to about 90 per cent (preferably about 85 per cent) of methanol or ethanol. The aqueous-alcoholic phase is separated, diluted with water, and extracted with an organic solvent which is partially miscible with water in which the triaryl-phosphonium salt is soluble (e.g., with ethyl acetate). The desired triaryl-phosphonium salt can be readily isolated in crystalline form from the resulting solution.

In a further reaction step the triaryl-phosphonium halide obtained is reacted with an unsaturated aldehyde to form a carotenoid. For this reaction aldehydes which are common in carotenoid chemistry can be employed. These aldehydes can also carry functional groups such as, for example, carbalkoxy residues, acetalized oxo groups, hydroxyl groups, or esterified hydroxyl groups.

Examples of unsaturated aldehydes useful herein include vitamin A aldehyde and aldehydes of the formula

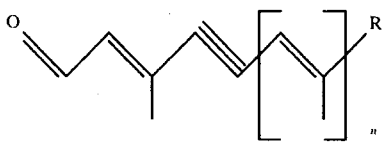

in which the dotted bond can be hydrogenated, $n = 0$ or 1, and R is carbalkoxy or an acetalized aldehyde. Examples of aldehydes within the above formula include 1,1-dialkoxy-(or 1,1-alkylenedioxy)-4-methyl-2,4-hexadien-6-al, 1,1-dialkoxy-(or 1,1-alkylenedioxy)-4-methyl-4-hexen-2-in-6-al, 4-methyl-6-oxo-2,4-hexadien-1-oic acid alkyl ester, 4-methyl-6-oxo-4-hexen-2-in-1-oic acid alkyl ester, 1,1-dialkoxy-(or 1,1-alkylenedioxy)-2,6-dimethyl-2,4,6-octatrien-8-al, 1,1-dialkoxy-(or 1,1-alkylenedioxy)-2,6-dimethyl-2,6-octadien-4-in-8-al, 2,6-dimethyl-8-oxo-2,4,6-octatrien-1-oic acid alkyl ester, 2,6-dimethyl-8-oxo-2,6-octadien-4-in-1-oic acid alkyl ester.

When R is carbalkoxy, carbolower alkoxy is preferred, and carbethoxy is most preferred. The alkoxy groups of the acetalized aldehyde group are preferably alkoxy groups having from 1 to 4 carbon atoms, most preferably, methoxy or ethoxy. The alkylenedioxy radical of the acetalized aldehyde group has preferably from 1 to 4 carbon atoms and is most preferably ethylenedioxy.

The proton acceptors employed in the reaction of the triaryl-phosphonium halide with the aldehyde component are preferably basic agents such as, for example, alkali metal hydroxides, alkaline-earth metal hydroxides, alkali metal amides, alkaline-earth metal amides, alkali metal alcoholates, alkaline-earth metal alcoholates, ammonia, strongly basic amines, metalorganic compounds such as, for example, lithium methyl, lithium phenyl, sodium phenyl, sodium methyl, Grignard compounds, etc.

The unsaturated aldehydes listed above can, for example, be prepared as follows:

2,6-Dimethyl-8-oxo-2,4,6-octatrien-1-oic acid ethyl ester

Trans 3-methyl-3-penten-1-in-5-ol is reacted with orthoformic acid ethyl ester. The resulting 1,1-diethoxy-4-methyl-4-hexen-2-in-6-ol is partially hydrogenated by means of a deactivated palladium catalyst, followed by treatment with hydrochloric acid to form 4-methyl-6-hydroxy-2,4-hexadien-1-al. Reaction with α-carbethoxy-ethylene-triphenyl-phosphoran yields 2,6-dimethyl-8-hydroxy-2,4,6-octatrien-1-oic acid ethyl ester, which can be oxidized by means of manganous oxide to 2,6-dimethyl-8-oxo-2,4,6-octatrien-1-oic acid ethyl ester.

1,1-Diethoxy-4-methyl-4-hexen-2-in-6-al

Trans 3-methyl-3-penten-1-in-5-ol and ortho-formic acid ethyl ester are reacted according to the above procedure to form 1,1-diethoxy-4-methyl-4-hexen-2-in-6-ol, which can be oxidized with manganous oxide to the corresponding aldehyde.

1,1-Diethoxy-2,6-dimethyl-2,4,6-octatrien-8-al

Trans 3-methyl-3-penten-1-in-5-ol is reacted by means of a Grignard reaction with methylmalondialdehyde enol ethyl ether, followed by treatment with acid to form 2,6-dimethyl-8-hydroxy-2,6-octadien-4-in-1-al. By partial hydrogenation of the latter compound there is formed 2,6-dimethyl-8-hydroxy-2,4,6-octatrien-1-al, which, after acylation of the free hydroxy group is converted into 1,1-diethoxy-2,6-dimethyl-8-acetoxy-2,4,6-octatrien-1-al by reaction with ortho-formic acid ethyl ester. Upon treatment with alkali, there is obtained the corresponding 8-hydroxy compound, which is then oxidized with manganous oxide to 1,1-diethoxy-2,6-dimethyl-2,4,6-octatrien-8-al.

1,1-Diethoxy-2,6-dimethyl-2,6-octadien-4-in-8-al

This aldehyde is obtained from trans 3-methyl-3-penten-1-in-5-ol and methylmalondialdehyde enol ethyl ether by means of the above reaction except for omission of the partial hydrogenation step.

EXAMPLE 1

50 parts by weight of vitamin A acetate mother liquor (obtained according to Helv. Chim. Acta, 1947, 30, p. 1923, abs. max. 328 m$\mu$, $E_1^1 = 553$) are dissolved in 500 parts by volume of ethanol and treated with a solution of 50 parts by weight of potassium hydroxide in 50 parts by volume of water. After standing for a half hour at room temperature, the solution is poured onto ice water and extracted with ether. The ether extract is dried over sodium sulfate after washing several times with water, filtered and evaporated in a vacuum. There are obtained 42.3 parts by weight of crude vitamin A alcohol.

The crude vitamin A alcohol is treated with 20 parts by weight of triphenyl-phosphine and 55 parts by volume of abs. ethanol. Thereafter, in a nitrogen atmosphere while stirring, 17 parts by volume of a methanolic hydrochloric acid solution (containing 162 mg. HCl/ml.) are added dropwise to the suspension thus obtained. The reaction mixture is left to stir for 60 hours at room temperature, then poured into water, and taken up in petroleum ether (40°–45°). The petroleum ether solution is extracted several times with 85 per cent methanol, whereby the intermediate phase which forms goes into solution. The methanol extract is washed in two further separating funnels with petroleum ether (40°–45°) and, after dilution with water, taken up in ethyl-acetate. The ethyl-acetate solution is washed with dilute aqueous sodium chloride solution, dried over sodium sulfate and evaporated in a vacuum. During the evaporation, crystallization of the retinyl-triphenyl-phosphonium chloride begins. There are obtained 22.6 parts by weight of (abs. max. 338 m$\mu$, $E_1^1 = 533$ in rectified alcohol) which can be purified further by recrystallization. From acetone or acetic ester there are obtained light yellow needles of melting point 192°–194° (abs. max. 262, 269, 276 and 340 m$\mu$, $E_1^1 = 181, 199, 214$ and 870).

EXAMPLE 2

Corresponding to the process of Example 1, from 44 parts by weight of a vitamin A mother liquor (manufactured by saponification of the concentrate obtainable in accordance with Helv. Chim. Acta, 1949, 32, p. 498, abs. max. 331 m$\mu$, $E_1^1 = 920$), which mainly contains 13-cis-vitamin A (the neo content amounts to 66.5 per cent in accordance with the maleic acid anhydride method, Vitamins and Hormones, 1960, 18, p. 315), and 25 parts by weight of triphenyl-phosphine in 60 parts by volume of abs. ethanol and 22 parts by volume of a methanolic hydrochloric acid solution (containing 162 mg. HCl/ml.), there are obtained 65.5 parts by volume of a crystalline product consisting of retinyl-triphenyl-phosphonium chloride which melts at 192°–194° after recrystallization from acetone.

EXAMPLE 3

After 60 hours stirring of 39 parts by weight of a vitamin A acetate mother liquor (manufactured according to Helv. Chim. Acta, 1949, 32, p. 498, abs. max. 328, $E_1^1 = 780$, mainly containing 13-cis-vitamin A acetate), 21 parts by weight of triphenylphosphine in 35 parts by volume of abs. ethanol and 18.5 parts by volume of methanolic hydrochloric acid (containing 162 mg. HCl/ml.), there are obtained, according to the procedure of Example 1, 52.3 parts by weight of a crystalline residue of retinyl-triphenyl-phosphonium chloride which melts at 192°–194° after recrystallization.

EXAMPLE 4

From 30 parts by weight of a vitamin A acetate mother liquor (obtained after carrying out a distribution operation of the oil obtained according to Helv. Chim. Acta, 1947, 30, 1923, abs. max. 298, 314 and 328, $E_1^1 = 601, 617$ and 538, $n_D^{25} = 1.5710$) in 40 parts by volume of abs. ethanol, 14 parts by weight of triphenyl-phosphine, and 14 parts by volume of methanolic hydrochloric acid (containing 162 mg. HCl/ml.) there are obtained after a 24 hour stirring at room temperature according to the process of Example 1, 7.1 parts by weight of crystalline retinyl-triphenyl-phosphonium chloride of melting point 192°–194°.

EXAMPLE 5

Following the process of Example 1, there are obtained from 15.5 parts by weight of a concentrate of vitamin A palmitate (prepared from natural vitamin A) by saponification with 15 parts by weight of potassium hydroxide in 15 parts by volume of water and 150 parts by volume of ethanol, 10.5 parts by weight of a vitamin A alcohol concentrate (abs. max. 325 m$\mu$, $E_1^1 = 750$). Thereafter, there are obtained by treatment with 5.5 parts by weight of triphenyl-phosphine in 15 parts by volume of absolute ethanol and 4.6 parts by weight of methanolic hydrochloric acid (containing 162 mg. HCl/ml.), 10.4 parts by weight of a crystalline residue of retinyl-triphenyl-phosponium chloride.

EXAMPLE 6

From 24 hours stirring of 37.5 parts by weight of triphenyl-phosphonium bromide with 50 parts by weight of the vitamin A used in Example 2 in 100 ml. of abs. ethanol there are obtained in a manner analogous to Example 1, 72.8 parts by weight of a crystalline residue of retinyl-triphenyl-phosphonium bromide. After repeated recrystallization from acetone, this compound melts at 180°–182° (abs. max. 261, 268, 276 and 340 m$\mu$, $E_1^1 = 148, 171, 188$ and 811).

EXAMPLE 7

18.9 parts by weight of 11,13-di-cis-vitamin A (abs. max. 314 m$\mu$, $E_1^1 = 902$, ca. 88 percent) give, after a 24 hour stirring with 78 parts by weight of triphenyl-phosphine in 30 parts by volume of abs. ethanol and 15.5 parts by volume of methanolic hydrochloric acid (containing 162 mg. HCl/ml.), corresponding to the process of Example 1, 32.3 parts by weight of a crystalline residue from which pure retinyl-triphenyl-phosphonium chloride of melting point 192°–194° is obtained by recrystallization.

EXAMPLE 8

52 parts by weight of a fish liver oil (Ocean-Gold, containing 7200 I.U. of vitamin per gram according to analysis) are saponified according to the process of Example 1. There are thus obtained 3 parts by weight of a vitamin A concentrate (abs. max. 323 m$\mu$, $E_1^1 = 70.7$). After the addition of 2 parts by weight of triphenyl-phosphine, 5 parts by volume of ethanol and 2.5 parts by volume of methanolic hydrochloric acid (containing 162 mg. HCl/ml.), the resulting mixture is stirred in a nitrogen atmosphere for 60 hours at room temperature. By working up according to the process of Example 1, there are obtained as the residue of the acetic ester extract 0.45 parts by weight of crude retinyl-triphenyl-phosphonium chloride. By recrystallization from acetic ester there is obtained 0.1 part by weight of crystalline retinyl-triphenyl-phosphonium chloride of melting point 186°–190°.

EXAMPLE 9

13.6 parts by weight of triphenyl-phosphonium chloride are dissolved in 100 parts by volume of absolute ethanol and, while stirring in a nitrogen atmosphere, simultaneously treated dropwise with a solution of 7 parts by weight of vitamin A aldehyde in 100 parts by volume of absolute ethanol and a solution of 0.6 parts by weight of sodium in 15 parts by volume of absolute methanol. After 2 hours the resulting red precipitate is filtered off, washed with water and dissolved in methylene chloride. The methylene chloride solution is filtered after drying over sodium sulfate and carefully evaporated. By spraying in ethanol there are obtained violet crystals of $\beta$-carotene. After recrystallization from benzene/ethanol, there are obtained 9.4 parts by weight of $\beta$-carotene of melting point 177°–179° (abs. max. 453, 480 m$\mu$, $E_1^1 = 2510, 2185$ in petroleum ether).

EXAMPLE 10

To a suspension of 31 g. of retinyl-triphenyl-phosphonium chloride and 10.5 g. of ethyl 2,6-dimethyl-8-oxo-2,4,6-octatrien-1-oate in 200 ml. of absolute benzene there is added dropwise, at room temperature and under nitrogen, a sodium ethylate solution prepared from 1.4 g. of sodium and 50 ml. of absolute ethanol. After the addition, the mixture is heated for 3 hours to 50°, cooled, and diluted with petroleum ether. The petroleum ether extract is washed with 85 percent aqueous methanol, and then with water, dried over sodium sulfate, filtered and concentrated under the vacuum of a water pump. 24.5 g. of ethyl all-trans $\beta$-apo-8′-carotenoate is obtained as a crystalline residue, which is recrystallized from benzene/ethanol. The mother liquors contain ethyl cis-$\beta$-apo-8′-carotenoate (abs. max. 326, 442 m$\mu$, $E_1^1 = 532, 1405$). By heating in high boiling petroleum ether and irradiating, there is obtained another portion of crystalline ethyl all-trans $\beta$-apo-8′-carotenoate. The united crystalline products are recrystallized from benzene/ethanol and give violet leaflets of melting point 135°–137°; abs. max. 445, 470 mµ ($E_1^1$ = 2500, 2110) (in petroleum ether).

The aldehyde used as starting material can be obtained as follows:

A Grignard solution is prepared in the usual manner from 61 g. of magnesium in 100 ml. of absolute tetrahydrofuran and 328 g. of ethyl bromide in 300 ml. of absolute tetrahydrofuran. The Grignard solution is diluted with 100 ml. of benzene and to it is added, at 0° and within 20 minutes, a solution of 112.5 g. of trans 3-methyl-2-penten-4-yn-1-ol in 400 ml. of benzene, whereupon the mixture is gently refluxed for 1 hours. To the refluxing solution there are added dropwise, within 1 hour, 180 g. of ethyl orthoformate and the solution is further stirred for 5½ hours under reflux. The mixture is poured onto 2 kg. of ice and 400 g. of ammonium chloride, separated and washed four times with 1 liter of water until neutral. The benzene solution is concentrated at 50° under the vacuum of a water pump and the residue distilled in high vacuo. The 1,1-diethoxy-4-methyl-4-hexen-2-yn-6-ol thus obtained boils at 130° (0.1 mm.) $n_D^{20}$ = 1.4826.

198 g. of 1,1-diethoxy-4-methyl-4-hexen-2-yn-6-ol are hydrogenated in the usual manner in the presence of 35 g. of a lead/palladium/calcium carbonate catalyst, 5 ml. of quinoline and 1500 ml. of high boiling petroleum ether. There is obtained 1,1-diethoxy-4-methyl-2,4-hexadien-6-ol of boiling point 96°–98° (0.01 mm.); $n_D^{20}$ = 1.4730 – 1.4760.

100 g. of 1,1-diethoxy-4-methyl-2,4-hexadien-6-ol are shaken for 20 minutes with 200 ml. of ether and 10 ml. of 3N hydrochloric acid and then treated with 20 g. of potassium carbonate, filtered, and the 4-methyl-6-hydroxy-2,4-hexadien-1-al, which is obtained almost quantitatively, is used without isolation in ethereal solution for the next step.

The ethereal solution of 4-methyl-6-hydroxy-2,4-hexadien-1-al obtained above is added dropwise within the space of 10 minutes with ice cooling to 180 g. of α-carbethoxy-ethlidene-triphenyl phosphorane in 200 ml. of methylene chloride and the resulting mixture refluxed for 3½ hours. The clear ethereal solution is washed three times, each time with 100 ml. of water, dried with sodium sulfate and concentrated at 50° in the vacuum of a water pump. The residue is dissolved in 200 ml. of isopropyl ether, cooled 3 hours at —20° and then separated by suction from the triphenyl-phosphine-oxide that crystallizes out, and the filtrate is concentrated at 50° under the vacuum of a water pump. There is thus obtained ethyl 2,6-dimethyl-8-hydroxy-2,4,6-octatrien-1-oate of boiling point 133°/0.03 mm.; $n_D^{20}$ = 1.5826.

22.5 g. of ethyl 2,6-dimethyl-8-hydroxy-2,4,6-octatrien-1-oate are dissolved in 300 ml. of ether and shaken for 16 hours at room temperature together with 110 g. of manganese dioxide. The mixture is filtered, thoroughly rinsed with ether, and the filtrate concentrated at 35° under the vacuum of a water pump. The residue is crystallized from petroleum ether (60°–90°)/ether. There is thus obtained 16.7 g. of ethyl 2,6-dimethyl-8-oxo-2,4,6-octatrien-1-oate as yellow needles of melting point 76°–77° showing absorption maxima at 316 and 330 mµ ($E_1^1$ = 2150 and 1885) (in petroleum ether).

EXAMPLE 11

To a suspension of 75 g. of retinyl-triphenyl-phosphonium chloride and 24.6 g. of 1,1-diethoxy-4-methyl-4-hexen-2-in-6-al in 300 ml. of absolute benzene at room temperature in a nitrogen atmosphere, there is added by dropping a sodium methylate solution formed from 3.3 g. of sodium and 100 ml. of absolute ethyl alcohol. The resulting mixture is heated for 2 hours at 50° C. and diluted after cooling with petroleum ether (boiling point 40°–50° C.). The petroleum ether extract is washed with 85 per cent aqueous methyl alcohol and water, and dried over potassium carbonate, and the solution filtered under reduced pressure (water pump). 55.5 g. of 11′,12′-dehydro-β-apo-10′-carotinaldiethyl acetal is obtained as an orange colored oil. (Abs. Max. 397, 417 mµ, $E_1^1$ = 1690, 1550).

The aldehyde employed as the starting material can be prepared according to the following procedure:

50 g. of 1,1-diethoxy-4-methyl-4-hexen-2-in-6-ol are dissolved in 1000 ml. of petroleum ether (boiling range 66°–90° C.) and, after the addition of 250 g. of manganous oxide, is shaken for 15 hours at room temperature. The resulting mixture is filtered, washed with ether, the solvent evaporated, and the residue obtained purified through distillation. 38 g. of 1,1-diethoxy-4-methyl-4-hexen-2-in-6-al is obtained; boiling point 84°–85° C./0.35 mm. Hg. (Abs. Max. 265 mµ; $E_1^1$ = 960).

EXAMPLE 12

To a suspension of 32 g. of retinyl-triphenyl-phosphonium chloride and 13 g. of 1,1-diethoxy-2,6-dimethyl-2,4,6-octatrien-8-al in 200 ml. of absolute benzene at room temperature in a nitrogen atmosphere, there is added a sodium ethylate solution prepared from 1.3 g. of sodium and 50 ml. of absolute ethanol. After the addition is completed, the resulting mixture is heated for 4 hours at 50° C. and, after cooling, diluted with petroleum ether. The petroleum ether extract is washed with 85 per cent aqueous methanol and water and dried over sodium sulfate, filtered, and the filtrate evaporated under reduced pressure. The resulting residue is dissolved in 300 ml. of acetone, 45 ml. of 3N sulfuric acid added thereto, and the solution allowed to stand for 1 hour at room temperature under a nitrogen atmosphere. Then the solution is diluted with water and extracted with ether. The eluate is washed with water, sodium bicarbonate solution, and water again, in that order, dried over sodium sulfate, filtered, and evaporated. 22.2 g. of residue (Abs. Max. 330, 453 mµ, $E_1^1$ = 560, 2470) (in petroleum ether) is obtained which is crystallized from petroleum ether (boiling point 60°–90° C.). From the mother liquor, containing the 15,15′-cis isomer, a further portion of crystalline all-trans β-apo-8′-carotinal, can be obtained by warming the mother liquor in high boiling petroleum ether (melting point 138°–139°; Abs. Max. = 456, 481 mµ, $E_1^1$ = 2650, 2200).

The aldehyde used as the starting material can be prepared as follows:

In the usual manner, a Grignard solution from 70 g. of magnesium in 200 ml. of absolute ether and 315 g. of ethyl bromide in 400 ml. of ether is prepared. To this solution at 0° under stirring in a nitrogen atmosphere, there is dropped in a solution of 127 g. of trans 3-methyl-3-penten-1-in-5-ol in 1400 ml. of methylene chloride. The reaction mixture is heated for ½ hour at the boiling point. Then at room temperature there is dropped in a solution of 136 g. of methylmalondialdehyde enol ethyl ether in 800 ml. of methylene chloride and the mixture heated for 2 hours at the boiling point. Then, to the cooled reaction mixture, there is added ice cold N-sulfuric acid. The methylene chloride extract is washed several times with water, dried over sodium sulfate, filtered, and evaporated under reduced pressure.

The residue obtained (240 g.) is dissolved in 1800 ml. of acetone, treated with 300 ml. of N-sulfuric acid and allowed to stand at room temperature in a nitrogen atmosphere for 1 hour. Then the reaction mixture, after dilution with 4000 ml. of water, is taken up in ether. The ether extract is washed with sodium bicarbonate solution and water, dried over sodium sulfate, filtered, and evaporated. 170 g. of crude 2,6-dimethyl-8-hydroxy-2,6-octadien-4-in-1-al is obtained which can be purified through adsorption on aluminum oxide (activity II deactivated by the addition of 7 per cent water). A small portion is removed by washing with petroleum ether/ether mixture (4:1). By elution with a petroleum ether/ether mixture (3:2) there is obtained pure 2,6-dimethyl-8-hydroxy-2,6-octadien-4-in-1-al (Abs. Max. 312 m$\mu$; $E_1^1 = 1200$) (in 96 per cent ethyl alcohol). 125 g. of 2,6-dimethyl-8-hydroxy-2,6-octadien-4-in-1-al are dissolved in 600 ml. of toluene and hydrogenated until the cessation of hydrogen takeup after the addition of 15 g. of a lead/palladium-calcium carbonate catalyst and 2 ml. of quinoline in the usual manner. After filtration and evaporation of the solution, there is obtained 2,6-dimethyl-8-hydroxy-2,4,6-octatrien-1-al.

55 g. of 2,6-dimethyl-8-hydroxy-2,4,6-octatrien-1-al are dissolved in 180 ml. of methylene chloride and 35 g. of pyridine added. Thereafter, at 0° under stirring in a nitrogen atmosphere, 33 g. of acetyl chloride in 50 ml. of methylene chloride is dropped in. The reaction mixture is stirred for an additional 2 hours at 8° C. Then the methylene chloride extract is washed with ice cold N-sulfuric acid, water, sodium bicarbonate solution, and water, dried over sodium sulfate, filtered, and evaporated under reduced pressure (water pump vacuum). The obtained crystalline cis-isomer of 2,6-dimethyl-8-acetoxy-2,4,6-octatrien-1-al is recrystallized from petroleum ether (boiling range 40°–45° C.)/ether mixture in yellow needles of melting point 42°–45° C.; yield, 66 g. (Abs. Max. 307 m$\mu$; $E_1^1 = 475$).

The cis-isomer of 2,6-dimethyl-8-acetoxy-2,4,6-octatrien-1-al can be isomerized as follows: 63 g. of aldehyde are dissolved in 150 ml. of absolute ether, and after the addition of 300 mg. of iodine, allowed to stand for 15 hours at room temperature in a nitrogen atmosphere. Then the reaction mixture is washed with n/10 sodium thiosulfate solution and water, dried over sodium sulfate, and filtered. After evaporation of the eluate, the residue obtained can be recrystallized from a petroleum ether/ether mixture. 2,6-Dimethyl-8-acetoxy-2,4,6-octatrien-1-al is thereby obtained in yellow needles of melting point 71°–72° C. (Abs. Max. 314 m$\mu$; $E_1^1 = 2180$). This product is the all-trans compound.

27.8 g. of 2,6-dimethyl-8-acetoxy-2,4,6-octatrien-1-al, which has not been isomerized with iodine, is reacted with 33 g. of orthoformic acid ethyl ester and a solution of 0.2 ml. of phosphoric acid and 100 mg. of p-toluenesulfonic acid in 15 ml. of ethyl alcohol. After standing at room temperature, 2 ml. of absolute pyridine is added thereto, and the mixture taken up in ether. The ether eluate is washed with sodium bicarbonate solution and water, dried over potassium carbonate, filtered, and evaporated under reduced pressure. The residue is dissolved in 250 ml. of methanol and after the addition of 20 g. of potassium hydroxide in 30 ml. of water, allowed to stand for 2 hours at room temperature in a nitrogen atmosphere. The reaction mixture is diluted with water, and then extracted with ether. The ether eluate is washed several times with water, then dried over potassium carbonate, filtered, and evaporated under reduced pressure. The crude 1,1-diethoxy-2,6-dimethyl-2,4,6-octatrien-8-ol (Abs. Max. 274 m$\mu$; $E_1^1 = 1235$) is employed without further purification for the next step.

31.1 g. of 1,1-diethoxy-2,6-dimethyl-2,4,6-octatrien-8-ol are dissolved in a mixture of 800 ml. of petroleum ether (boiling range 40°–45° C.) and 200 ml. of ether, and after the addition of 150 g. of manganous oxide, shaken for 16 hours at room temperature. The mixture is then filtered, washed with ether, and after evaporation of the filtrate, 22 g. of 1,1-diethoxy-2,6-dimethyl-2,4,6-octatrien-8-al is obtained, which can be used for the Wittig reaction without further purification. The aldehyde can be purified through adsorption on aluminum oxide (activity II deactivated with 2 per cent water and 0.5 per cent pyridine). A small portion is removed by washing with a petroleum ether/ether mixture (95:5). By elution with a petroleum ether/ether mixture (3:1), there is obtained pure 1,1-diethoxy-2,6-dimethyl-2,4,6-octatrien-8-al (Abs. Max. 325 m$\mu$; $E_1^1 = 1200$; $n_D^{24} = 1.5607$). Melting point of the di-semicarbazone 242°–243° C. with decomposition.

EXAMPLE 13

Another condensation component is 1,1-diethoxy-2,6-dimethyl-2,6-octadien-4-in-8-al, which can be reacted with retinyl-triphenyl-phosphonium chloride to give 11',12'-dehydro-$\beta$-apo-8'-carotinaldiethyl acetal.

The 1,1-diethoxy-2,6-dimethyl-2,6-octadien-4-in-8-al can be prepared as follows:

43 g. of 2,6-dimethyl-8-hydroxy-2,6-octadien-4-in-1-al are dissolved in 50 ml. of methylene chloride and 26 g. of pyridine. To this solution at 0° under stirring in a nitrogen atmosphere is dropped 25 g. of acetyl chloride in 50 ml. of methylene chloride. The mixture is stirred for 1 hour at 0°, poured into ice cold n-sulfuric acid, and taken up in ether. The ether extract is washed seriatim with water, sodium bicarbonate solution, and water, then dried over sodium sulfate, and filtered. After evaporation, the residual 2,6-dimethyl-8-acetoxy-2,6-octadien-4-in-1-al (50.6 g.) can be distilled under high vacuum, boiling point 101°–102° C./0.03 mm. (Abs. Max. 304 m$\mu$; $E_1^1 = 1110$; $n_D^{22} = 1.5592$).

36 g. of 2,6-dimethyl-8-acetoxy-2,6-octadien-4-in-1-al is reacted with 31 g. of orthoformic acid ethyl ester and a solution of 0.3 ml. of phosphoric acid and 150 mg. of p-toluenesulfonic acid in 20 ml. of absolute methanol. After standing for 20 hours at room temperature in a nitrogen atmosphere, 2 ml. of absolute pyridine is added and the reaction mixture taken up in ether. The ether extract is washed with sodium bicarbonate solution and water, dried over potassium carbonate, filtered and evaporated under reduced pressure (water pump vacuum). 48 g. of 1,1-diethoxy-2,6-dimethyl-8-acetoxy-2,6-octadien-4-in is obtained (Abs. Max. 269 m$\mu$; $E_1^1 = 730$).

48 g. of 1,1-diethoxy-2,6-dimethyl-8-acetoxy-2,6-octadien-4-in is dissolved in 250 ml. of methanol and reacted with a solution of 25 g. of potassium hydroxide in 40 ml. of water. After standing for 2 hours at room temperature, the mixture is diluted with water and extracted with ether. The ether extract is washed several times with water, dried over potassium carbonate, and filtered. After evaporation of the solvent, there remains behind 40.5 g. of crude 1,1-diethoxy-2,6-dimethyl-2,6-octadien-4-in-8-ol (Abs. Max. 268 mµ; $E_1^1 = 790$), which can be used in the next step without further purification.

The 1,1-diethoxy-2,6-dimethyl-2,6-octadien-4-in-8-ol obtained above is dissolved in 1000 ml. of petroleum ether (boiling range 60°–90° C.), 200 g. of manganous oxide added, and the resulting mixture shaken for 15 hours at room temperature. The mixture is then filtered, washed with ether, and the filtrate evaporated. 32 g. of 1,1-diethoxy-2,6-dimethyl-2,6-octadien-4-in-8-al is obtained, which can be purified by distillation or through adsorption on aluminum oxide (activity II deactivated with 2 per cent water and 0.5 per cent pyridine). The aldehyde is obtained as a bright yellow oil when eluted from an aluminum oxide column with a petroleum ether/ether mixture (9:1); boiling point 92°/0.01 mm.; $n_D^{23} = 15267$ (Abs. Max. $E_1^1 = 665$).

We claim:

1. A compound of the formula:

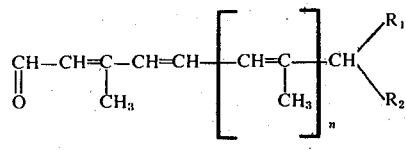

wherein
n is an integer 0 or 1;
$R_1$ and $R_2$ individually are alkoxy containing from 1 to 4 carbon atoms; and $R_1$ and $R_2$ taken together form the ethylenedioxy group.

2. The compound of claim 1 wherein said compound is 1,1-dilower alkoxy-4-methyl-2,4-hexadien-6-al.

3. The compound of claim 1 wherein said compound is 1,1-diethoxy-4-methyl-2,4-hexadien-6-al.

4. The compound of claim 1 wherein said compound is 1,1-dilower alkoxy-2,6-dimethyl-2,4,6-octatrien-8-al.

5. The compound of claim 1 wherein said compound is 1,1-diethoxy-2,6-dimethyl-2,4,6-octatrien-8-al.

* * * * *